(12) United States Patent
Scheffer

(10) Patent No.: US 7,659,517 B2
(45) Date of Patent: Feb. 9, 2010

(54) METHOD AND APPARATUS FOR TRIGGERING IMAGE ACQUISITION IN RADIOGRAPHY

(75) Inventor: Danny Scheffer, Hulst (NL)

(73) Assignee: Cypress Semiconductor Corporation, San Jose, CA (US)

(*) Notice: Subject to any disclaimer, the term of this patent is extended or adjusted under 35 U.S.C. 154(b) by 239 days.

(21) Appl. No.: 11/701,123

(22) Filed: Jan. 31, 2007

(65) Prior Publication Data

US 2008/0179531 A1 Jul. 31, 2008

(51) Int. Cl.
*H01L 27/146* (2006.01)
*G01T 1/16* (2006.01)

(52) U.S. Cl. .......................... 250/370.09; 250/370.11; 378/98.8

(58) Field of Classification Search ............ 250/370.09, 250/370.11; 378/98.8; 257/59, 239, 291, 257/292
See application file for complete search history.

(56) References Cited

U.S. PATENT DOCUMENTS

| 5,471,515 A | 11/1995 | Fossum et al. |
| 5,887,049 A | 3/1999 | Fossum |
| 2004/0026623 A1* | 2/2004 | Doty et al. ............. 250/370.09 |
| 2004/0065836 A1 | 4/2004 | Schick et al. |
| 2007/0176109 A1* | 8/2007 | Bell ..................... 250/370.09 |

OTHER PUBLICATIONS

Fossum, E. R., R. H. Nixon, and D. Schick. "A 37x28mm 600k-Pixel CMOS APS Dental X-Ray Camera-on-a-Chip with Self Triggered Readout". ISSCC98, Session 11: Image Sensors, Paper FA 11.3, Feb. 6, 1998.*
Wikipedia "Active pixel sensor," <http://en.wikipedia.org/wiki/Active_pixel_sensor>; retrieved Dec. 7, 2006; 4 pages.

* cited by examiner

*Primary Examiner*—David P Porta
*Assistant Examiner*—Casey Bryant

(57) ABSTRACT

An apparatus for triggering image acquisition in radiography includes an interconnect, a detector to detect radiation and a switch coupled between the interconnect and the detector to charge the interconnect in response to the radiation while the switch is in an open-circuit state. The apparatus also includes control circuitry coupled to the interconnect to detect the charge on the interconnect and to generate a signal indicating presence of the radiation in response to the charge. A method for triggering image acquisition in radiography includes coupling a switch between an interconnect and a detector, then charging an interconnect with that switch in response to radiation incident upon the switch while the switch is in an open-circuit state. Next, the charge on the interconnect is monitored and a signal is generated indicating the presence of the radiation in response to that charge.

19 Claims, 7 Drawing Sheets

METHOD AND APPARATUS FOR TRIGGERING IMAGE ACQUISITION IN RADIOGRAPHY

TECHNICAL FIELD

This disclosure relates generally to radiography, and in particular but not exclusively, relates to triggering image acquisition in filmless radiography.

BACKGROUND INFORMATION

Dentists, orthodontists, periodontists, and oral surgeons typically use electromagnetic radiation (e.g., x-rays) to obtain images of a patient's teeth, mouths and gums to aid in diagnosis and treatment. In traditional oral and dental radiography, a photographic film is placed in the patient's mouth, for example behind a patient's tooth, and an x-ray beam is projected through the tooth and onto the film. The film, after being exposed, is developed in a dark room or a closed developer using special chemicals to obtain a photographic image of the tooth.

Recently, the field of filmless dental radiography has emerged. In filmless dental radiography, an x-ray beam is still projected through the patient's tooth, but no photographic film is used. Instead, an electronic sensor is placed in the patient's mouth behind the tooth to be examined. The electronic sensor may include a charge-coupled device (CCD), a complementary metal-oxide semiconductor (CMOS) active pixel sensor (APS) array or any other filmless radiation sensor. The x-rays pass through the tooth and impinge on the electronic sensor, which converts the x-rays into an electrical signal. The electrical signal is then transmitted to a computer to produce an image on an associated output device, such as a monitor or a printer.

Minimizing the patient's exposure to x-rays and obtaining an accurate image are of concern when using a filmless dental radiography system. These systems typically utilize an x-ray source and an intraoral sensor. In these systems, it is often desirable to maximize the sensitivity of the sensor so that a short x-ray pulse can be used to minimize the patient's exposure time. However, the x-ray source and the sensor are often sold as separate components with, typically, no communicative link between them. Thus, the radiography system cannot tell when to begin the image acquisition process (i.e., the sensor cannot tell when x-rays are being emitted from the source).

One approach to this problem has been for the radiography system to acquire a partial frame of an image that is output by the intraoral sensor. The system then digitally analyzes the partial frame and checks the average grey level of the image. If the grey level changes beyond a set threshold the system can assume that x-rays are present and it can begin a full frame capture. The drawback of this approach is that it takes additional time and uses a significant portion of the x-ray pulse (e.g., 10-20%), thereby increasing the time a patient is exposed to radiation. Since a significant portion of the x-ray pulse is used to detect the presence of the radiation, there is less time available to acquire the actual image. Therefore, the patient's radiation dose is often increased.

Another approach to this problem has been to add diodes in the corners of the intraoral sensor to detect the presence of x-rays. However, this approach could prove inadequate because the diodes do not cover the entire field of view, resulting in missed x-ray pulses. The more missed pulses, the higher the patient's dosage of radiation is needed before the x-rays are detected and an image is acquired.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

DETAILED DESCRIPTION

Embodiments of a method and apparatus for triggering image acquisition in filmless radiography are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
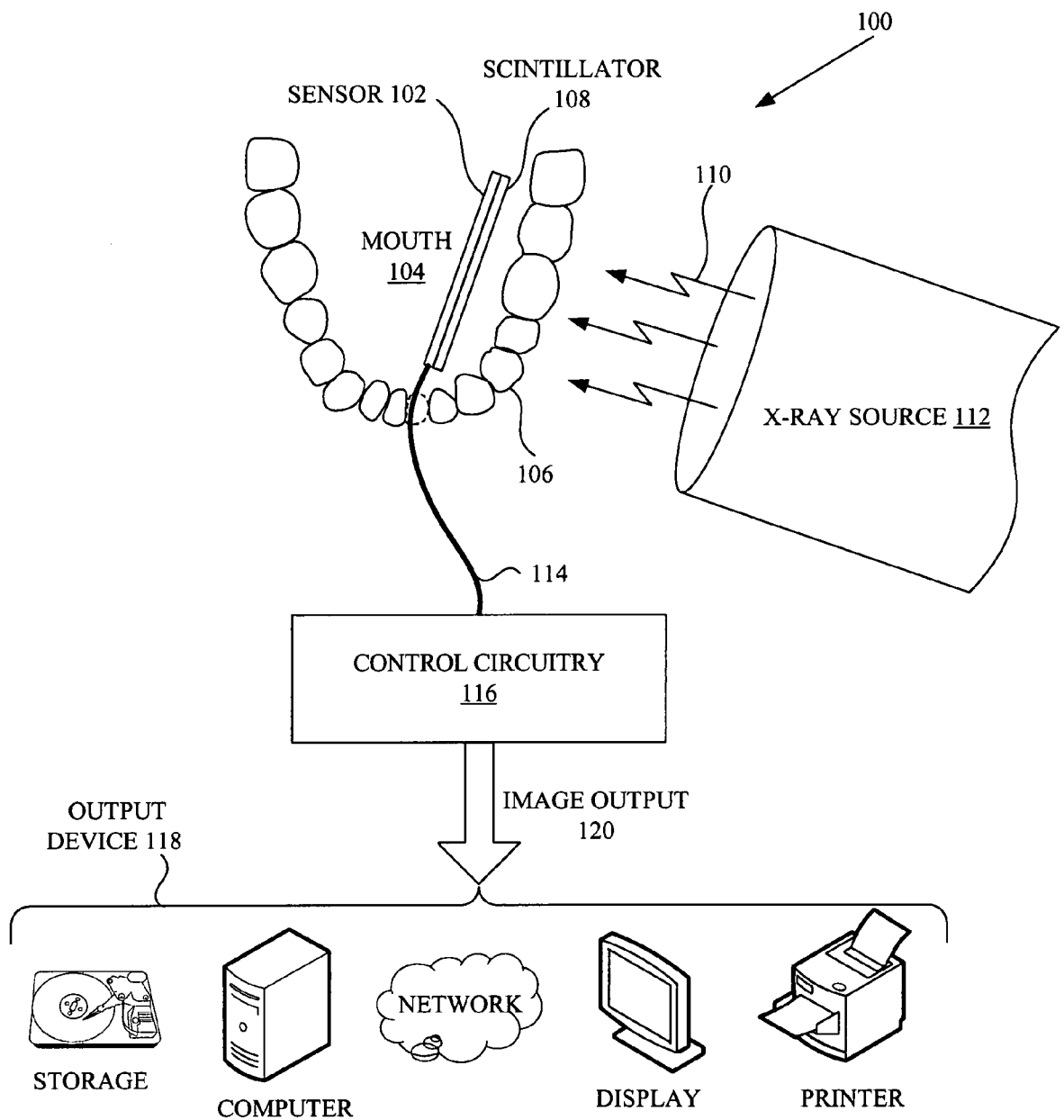
FIG. 1 is a block diagram illustrating a demonstrative filmless dental radiography system, in accordance with an embodiment of the invention.

FIG. 1 is a block diagram illustrating a demonstrative filmless dental radiography system 100 in accordance with an embodiment of the invention. The illustrated embodiment of radiography system 100 includes sensor 102, scintillator 108, x-ray source 112, link 114, control circuitry 116 and output devices 118.

In the illustrated embodiment, sensor 102 is placed inside a patient's mouth 104 behind teeth 106 to be examined. X-ray source 112 emits electromagnetic radiation 110, which passes through teeth 106 and impinges on sensor 102, which converts electromagnetic radiation 110 into an electrical signal. Sensor 102 may optionally include a scintillator 108 disposed proximate to sensor 102 to translate electromagnetic radiation 110 from a first wavelength to a second wavelength. For example, scintillator 108 may absorb electromagnetic or charged particle radiation, then in response, fluoresce at a characteristic wavelength that is detectable by sensor 102. In one embodiment, electromagnetic radiation 110 includes x-ray radiation and scintillator 108 fluoresces light in the visible spectrum. The fluoresced visible light is then detected by sensor 102.

In the illustrated embodiment, control circuitry 116 is coupled to sensor 102 via a link 114. Control circuitry 116 is configured to automatically detect the presence of electromagnetic radiation 110, trigger the acquisition of image output 120, and to control the read-out of data from sensor 102. Although FIG. 1 illustrates control circuitry 116 as external to sensor 102, in alternative embodiments, all or a portion of control circuitry may be incorporated directly onto sensor 102. In addition, although link 114 is shown in FIG. 1 as a wired link, it is recognized that a wireless link may be used to communicate control or image data between sensor 102 and control circuitry 116 or between sensor 102 and output device 118. In one embodiment, sensor 102 may include an antenna to transmit image output 120 via a wireless link to output device 118.

Output device 118 includes any device for displaying, storing, transmitting, or manipulating image output 120. By way of example, output device 118 may include a data storage unit (e.g. hard drive), a computer, a network, a user display (e.g. monitor), a printer, and the like.

Although the illustrated embodiment of FIG. 1 shows radiography system 100 as applied to dental filmless radiography, it is not intended to limit the invention to the field of dental filmless radiography, but instead is provided as an illustrative embodiment of a method and apparatus for triggering image acquisition in radiography, in general. For example, embodiments of the invention could be used in general medical radiography such as, hard and soft tissue radiography, mammography, angiography, gastrointestinal fluoroscopy, and the like. Even still, embodiments of the invention could be used in industrial radiography applications, such as, non-destructive testing (NDT) or airport security and the like.

Figure 2:
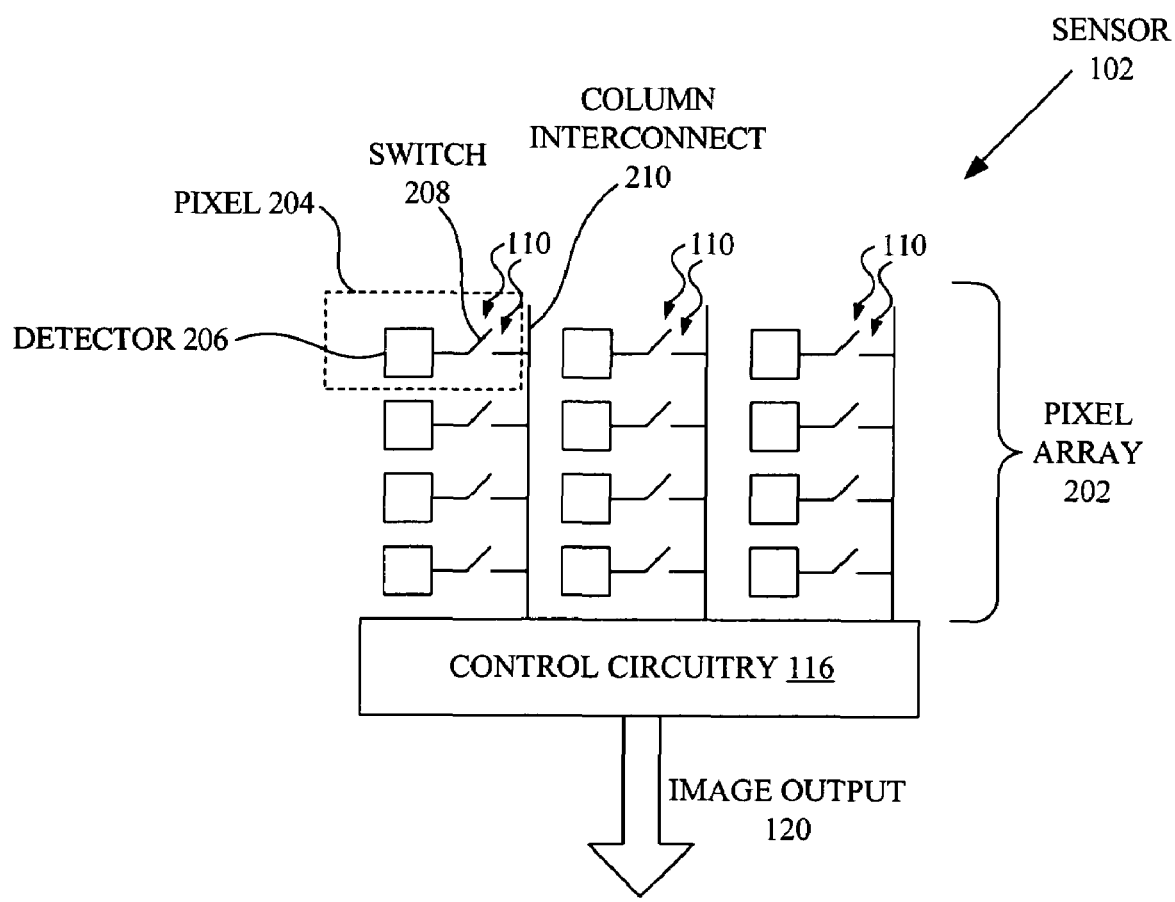
FIG. 2 is a functional block diagram illustrating a sensor of a filmless radiography system, in accordance with an embodiment of the invention.

FIG. 2 is a functional block diagram illustrating sensor 102 of filmless radiography system 100, in accordance with an embodiment of the invention. The illustrated embodiment of sensor 102 includes a pixel array 202 having a plurality of pixels 204 coupled to control circuitry 116 via column interconnects 210. Pixel 204 includes a detector 206 coupled to column interconnect 210 via switch 208.

Figure 3:
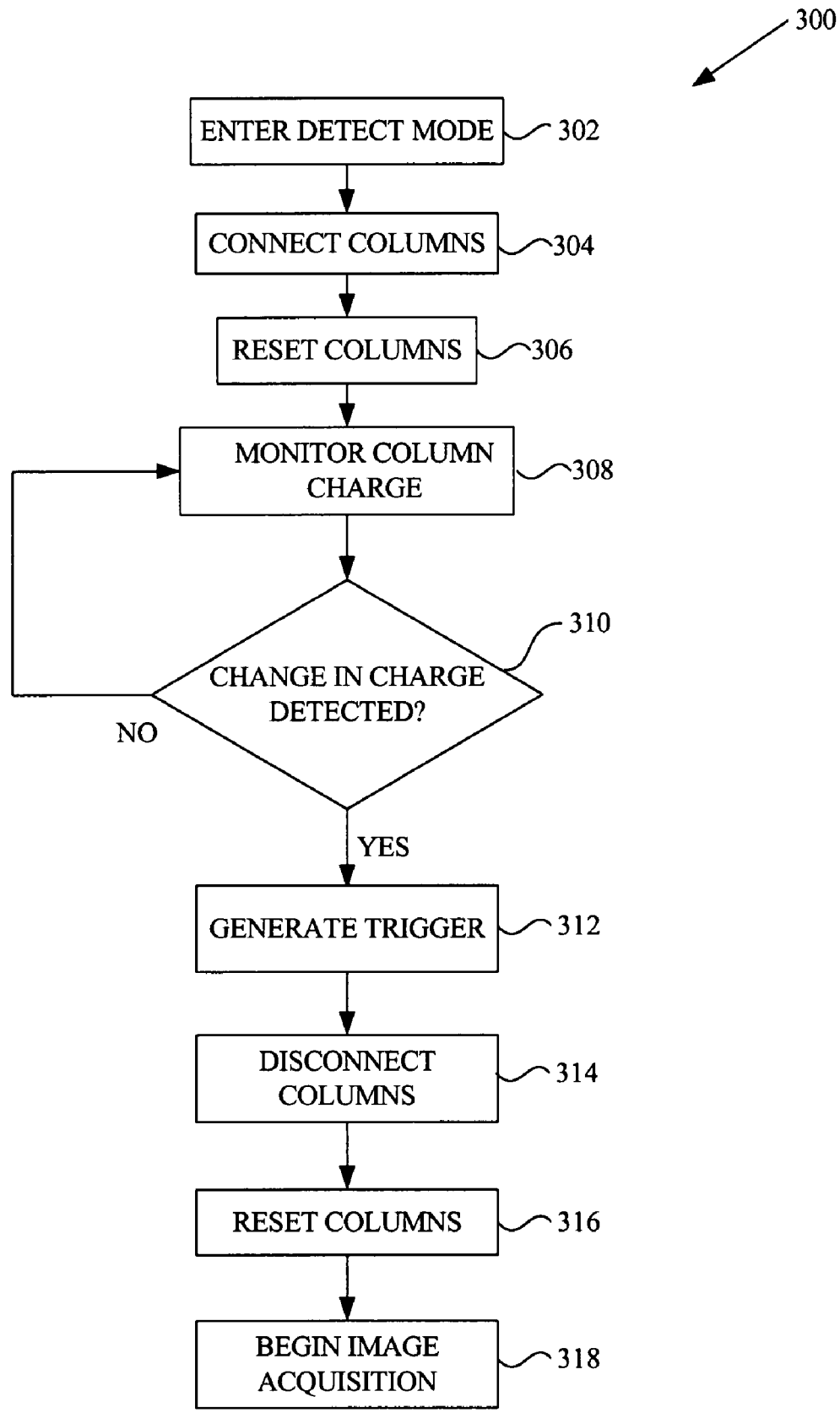
FIG. 3 is a flow chart illustrating a process for triggering image acquisition in filmless radiography, in accordance with an embodiment of the invention.

FIG. 3 is a flow chart illustrating a process 300, executed by sensor 102 and control circuitry 116, in accordance with an embodiment of the invention. Process 300 is described with reference to FIGS. 2 and 3. The order in which some or all of the process blocks appear in process 300 should not be deemed limiting. Rather, one of ordinary skill in the art having the benefit of the present disclosure will understand that some of the process blocks may be executed in a variety of orders not illustrated.

In a process block 302, control circuitry 116 enters a detect mode to detect the presence of electromagnetic radiation. In one embodiment, control circuitry 116 puts switches 208 in an open-circuit state (i.e., opens the switches) in response to entering the detect mode.

In a process block 304, control circuitry 116 optionally connects one or more of column interconnects 210 to one another. The connected column interconnect 210 creates a single column output that can be monitored in order to detect the presence of electromagnetic radiation 110. In an alternative embodiment, each column interconnect 210 can be monitored separately for a more localized detection of electromagnetic radiation 110.

In a process block 306, control circuitry 116 resets any charge already accumulated on column interconnect 210. In one embodiment, control circuitry 116 resets the charge by temporarily grounding column interconnect 210. In another embodiment, control circuitry 116 resets the charge by charging the column interconnect 210 to a predetermined level.

In a process block 308, control circuitry 116 monitors the charge on column interconnect 210. In a process block 310, if no change is detected in the charge on column interconnect 210, process 300 reverts back to process block 308 to continue monitoring the charge, provided control circuitry 116 is still in the detect mode. If electromagnetic radiation 110 is present, switch 208 will charge column interconnect 210 in response to electromagnetic radiation 110 incident upon switch 208.

In response to a threshold change in the charge on column interconnect 210, control circuitry 116 generates a trigger in a process block 312. Typically electromagnetic radiation 110 incident upon switch 208 will result in an abrupt voltage level transition on column interconnect 210, though other signal types and waveforms can be detected by control circuitry 116 to generate the trigger. Control circuitry 116 then exits the detect mode by disconnecting column interconnects 210 from one another and resetting the charge in a process block 316. As with the reset above, process block 316 may reset column interconnect 210 by temporarily connecting column interconnect 210 to ground or by introducing a predetermined charge onto column interconnect 210.

In a process block 318, control circuitry 116 then initiates the image acquisition process and selectively enables pixel 204 by changing switch 208 to a closed-circuit state (i.e. close the switch) and then reads an output from detector 206 to acquire an image output 120.

Figure 4:
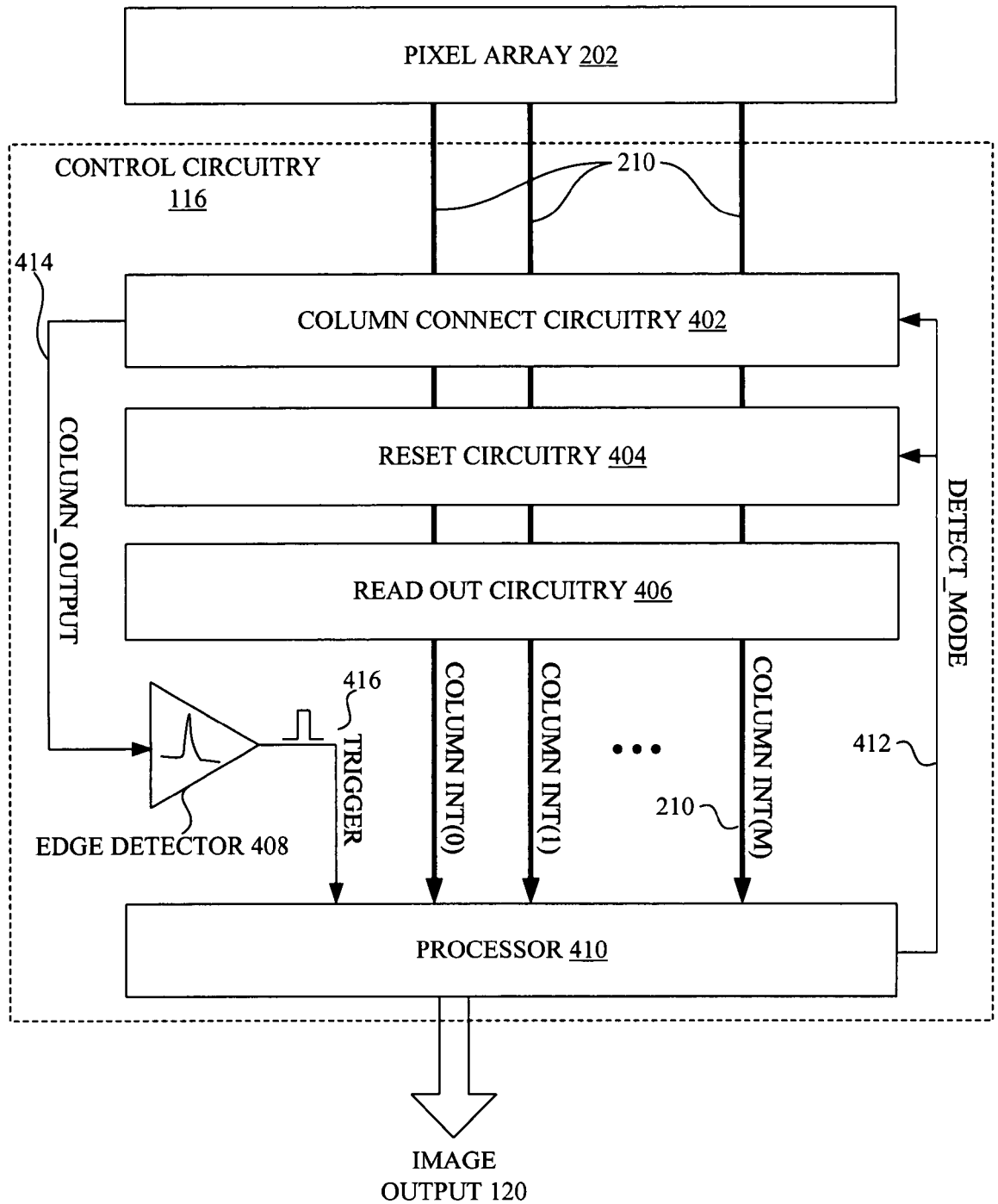
FIG. 4 is a functional block diagram illustrating a sensor of a filmless radiography system, in accordance with an embodiment of the invention.

FIG. 4 is a functional block diagram illustrating control circuitry 116 of a filmless radiography system 100, in accordance with an embodiment of the invention. The illustrated embodiment of control circuitry 116 includes column connect circuitry 402, reset circuitry 404, read-out circuitry 406, edge detector 408, and processor 410.

In the illustrated embodiment, column connect circuitry 402 is coupled to connect column interconnects 210 to one another in response to a DETECT_MODE signal 412 generated by processor 410. Column connect circuitry 402 is also coupled to generate a COLUMN_OUTPUT signal 414. In one embodiment, COLUMN_OUTPUT signal 414 represents a combined charge of all column interconnects 210. In another embodiment, COLUMN_OUTPUT signal 414 represents a charge on one or more of column interconnects 210. In one embodiment, COLUMN_OUTPUT signal 414 can represent a voltage on one or more of column interconnects 210.

Reset circuitry 404 is coupled to reset the charge on column interconnects 210 in response to receiving the DETECT_MODE signal 412 from processor 410. As stated above, reset circuitry 404 may reset the charge by temporarily grounding column interconnect 210 or by charging it to a predetermined level. In an alternative embodiment, reset circuitry 404 may reset column interconnects 210 by temporarily applying a voltage to column interconnects 210. In one embodiment, reset circuitry 404 is also coupled to reset column interconnects 210 in response to a detection of electromagnetic radiation prior to image acquisition.

Edge detector 408 is coupled to receive COLUMN_OUTPUT signal 414. Edge detector 408 monitors COLUMN_OUTPUT signal for changes that indicate a change in charge on column interconnect 210. If a change is detected, edge detector 408 generates a TRIGGER signal 416 that indicates the presence of electromagnetic radiation. In one embodiment, edge detector 408 generates TRIGGER signal 416 in response to a spike in charge on column interconnect 210. In another embodiment, TRIGGER signal 416 is generated when the charge on column interconnect 210 exceeds a threshold level. In still another embodiment, TRIGGER signal 416 is generated when a rate at which the charge increases on column interconnect exceeds a threshold level. By way of example, edge detector 408 may monitor the voltage level of column interconnects 210 in similar manners as those described with the monitoring of the charge.

Processor 410 is coupled to receive TRIGGER signal 416 generated by edge detector 408. In response to receiving TRIGGER signal 416, processor 410 is configured to exit detect mode and enter an image acquisition mode. Upon entering image acquisition mode, column connect circuitry 402 disconnects column interconnects 210 and reset circuitry 404 resets the accumulated charge. Then, read-out circuitry 406 selectively enables each pixel of pixel array 202 and reads an output from each. The collective output is then assembled by processor 410 to produce image output 120. Although FIG. 4 illustrates processor 410 as part of control circuitry 116, in an alternative embodiment, processor 410 may be separate from control circuitry 116 and may even be located on a separate device from sensor 102, such as one of the output devices 118 indicated in FIG. 1.

Figure 5:
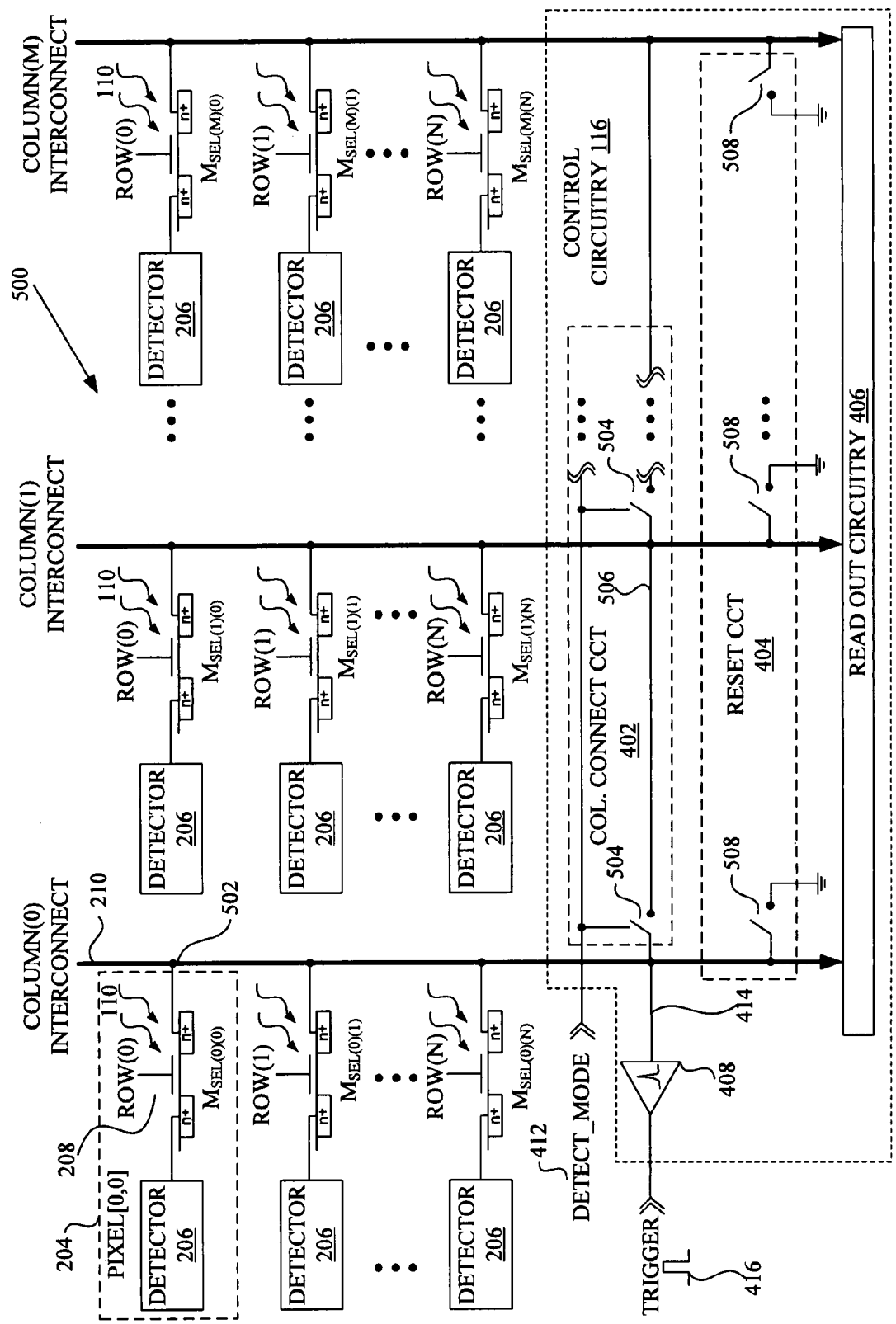
FIG. 5 is a circuit diagram illustrating a sensor of a filmless radiography system, in accordance with an embodiment of the invention.

FIG. 5 is a circuit diagram illustrating a sensor 500 of a filmless radiography system, in accordance with an embodiment of the invention. Sensor 500 is one possible embodiment of sensor 102, shown in FIGS. 1 and 2. The illustrated embodiment of sensor 500 includes pixels 204, column interconnects 210 and control circuitry 116. Pixels 204 include detector 206 and switch 208. Control circuitry 116 includes column connect circuitry 402, reset circuitry 404, and read-out circuitry 406. Column connect circuitry 402 includes switches 504 and bus 506. Reset circuitry 404 includes switches 508.

In the illustrated embodiment, switch 208 is depicted as an n-type metal oxide semiconductor field effect transistor ("nMOSFET") coupled between column interconnect 210 and detector 206. One function of switch 208 is to act as a row select switch to enable and disable detector 206 by connecting and disconnecting detector 206 to and from interconnect 210. However, when switch 208 is in an open-circuit state (e.g., gate at 0V potential), the drain of switch 208 is still connected to column interconnect 210. A junction 502 between the drain of switch 208 and column interconnect 210 results in essentially an nplus-p-substrate photodiode which is light sensitive. In one embodiment, by connecting all column interconnects 210 while switches 208 are in an open-circuit state results essentially in a distributed photodiode over the entire image plane of sensor 500. Using the parasitic light sensitivity of switches 208 allows for full coverage of pixel array 202 for the detection of the presence of electromagnetic radiation 110.

Column connect circuitry 402 is coupled to receive DETECT_MODE signal 412 from processor 410 (shown in FIG. 4). In the illustrated embodiment, in response to receiving DETECT_MODE signal 412, column connect circuitry 402 closes switches 504 to connect column interconnects 210 together via bus 506. Bus 506 is coupled to edge detector 408 to propagate COLUMN_OUTPUT signal 414. In one embodiment, column connect circuitry 116 can selectively close one or more of switches 504 to connect one or more of column interconnects 210.

In the illustrated embodiment, reset circuitry 404 includes switches 508 to temporarily connect column interconnects 210 to ground. In an alternative embodiment, switches 508 may be configured to connect column interconnect to a voltage source to apply a predetermined voltage to column interconnect 210.

Read-out circuitry 406 is coupled to selectively enable each pixel 204 and then read an output from its respective detector 206. For ease of illustration, pixels 204 of pixel array 202 are described as arranged in terms of ROWS and COLUMNS. However, it is recognized that pixel array 202 may be arranged in any logical configuration for selective addressing of pixels 204. In one embodiment read-out circuitry reads an output from pixel[0,0] [i.e. COLUMN(0), ROW(0)], by first applying a voltage to ROW(0) to close switch 208 of pixel[0, 0]. Read-out circuitry 406 then reads an output from pixel[0, 0] via column(0) interconnect 210. Read-out circuitry 406 may then disable pixel[0,0] by removing the voltage from ROW(0) and select another pixel 204 for read-out.

Figure 6:
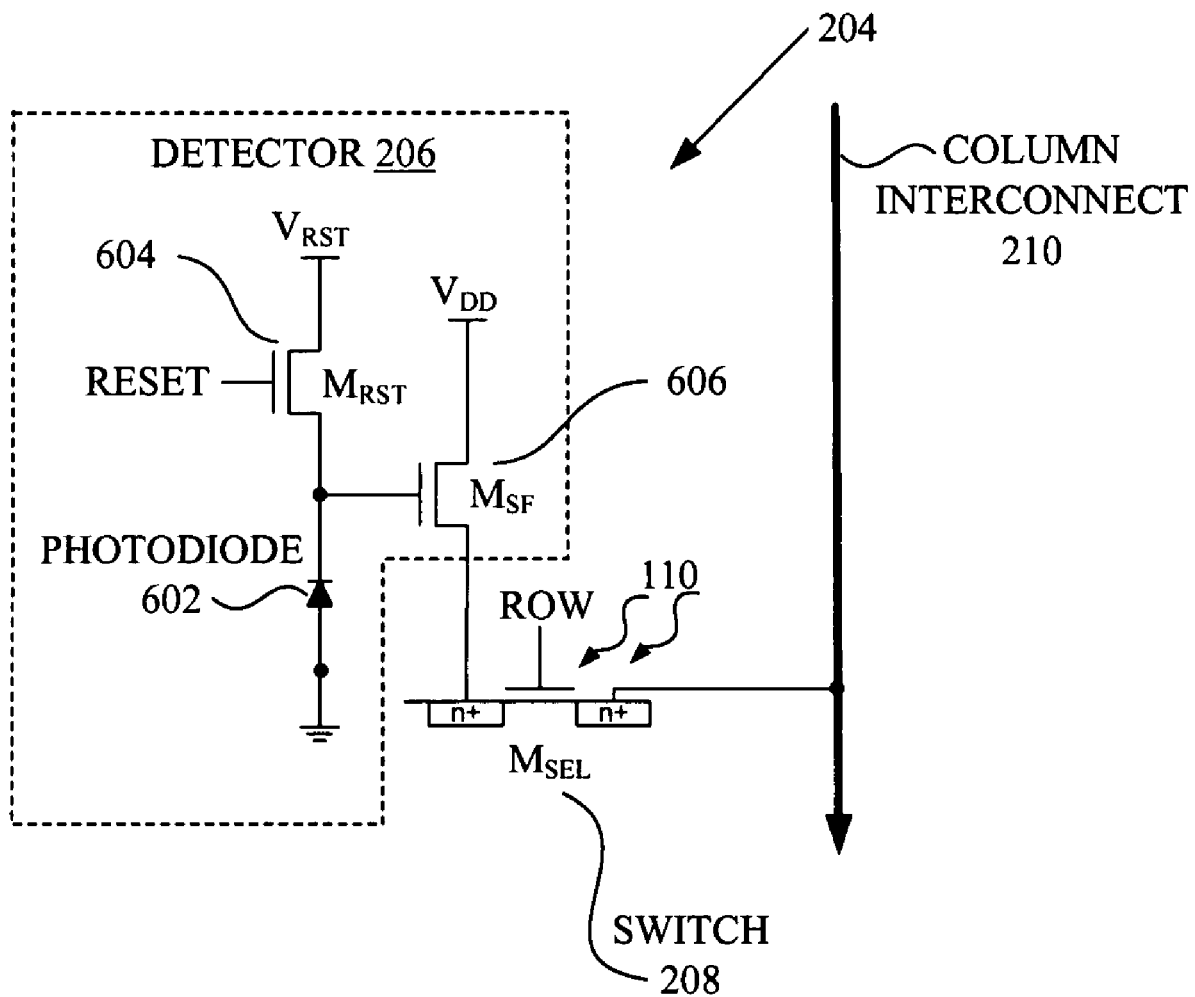
FIG. 6 is a circuit diagram illustrating one pixel of a sensor of a filmless radiography system, in accordance with an embodiment of the invention.

FIG. 6 is a circuit diagram illustrating a pixel 204 of sensor 500 of a filmless radiography system, in accordance with an embodiment of the invention. The illustrated embodiment of pixel 204 includes a detector 206 and switch 208 (e.g., nMOSFET). Detector 206 includes photodiode 602, a reset transistor 604, and a buffer transistor 606.

In the illustrated embodiment of detector 206, electromagnetic radiation incident upon photodiode 602 causes an accumulation of charge on the 'parasitic' capacitance of photodiode 602, creating a voltage change related to the incident radiation. In one embodiment, a photogate detector (not shown) can be used instead of photodiode 602.

Reset transistor 604 is coupled to reset photodiode 602. In one embodiment, a drain of reset transistor is coupled to a voltage source (VRST). When reset transistor 604 is turned on via a RESET signal applied to its gate, photodiode 602 is effectively connected to VRST resetting the integrated charge.

Buffer transistor 606 is coupled to act as an amplifier which allows the voltage on photodiode 602 to be measured without removing the accumulated charge. In one embodiment, the drain of buffer transistor 606 is tied to a voltage source (VDD). By way of example, the drain of buffer transistor 606 can be tied to the power supply VRST of reset transistor 604.

Although the illustrated embodiment of pixel 204 includes only 3 transistors, other configurations of pixel 204 can include four or more transistors, such as 4T, 5T and 6T active pixel array arrangements. For example, by adding an extra transistor as in a 4T active pixel arrangement, a transfer gate is added to enable correlated double sampling.

Figure 7:
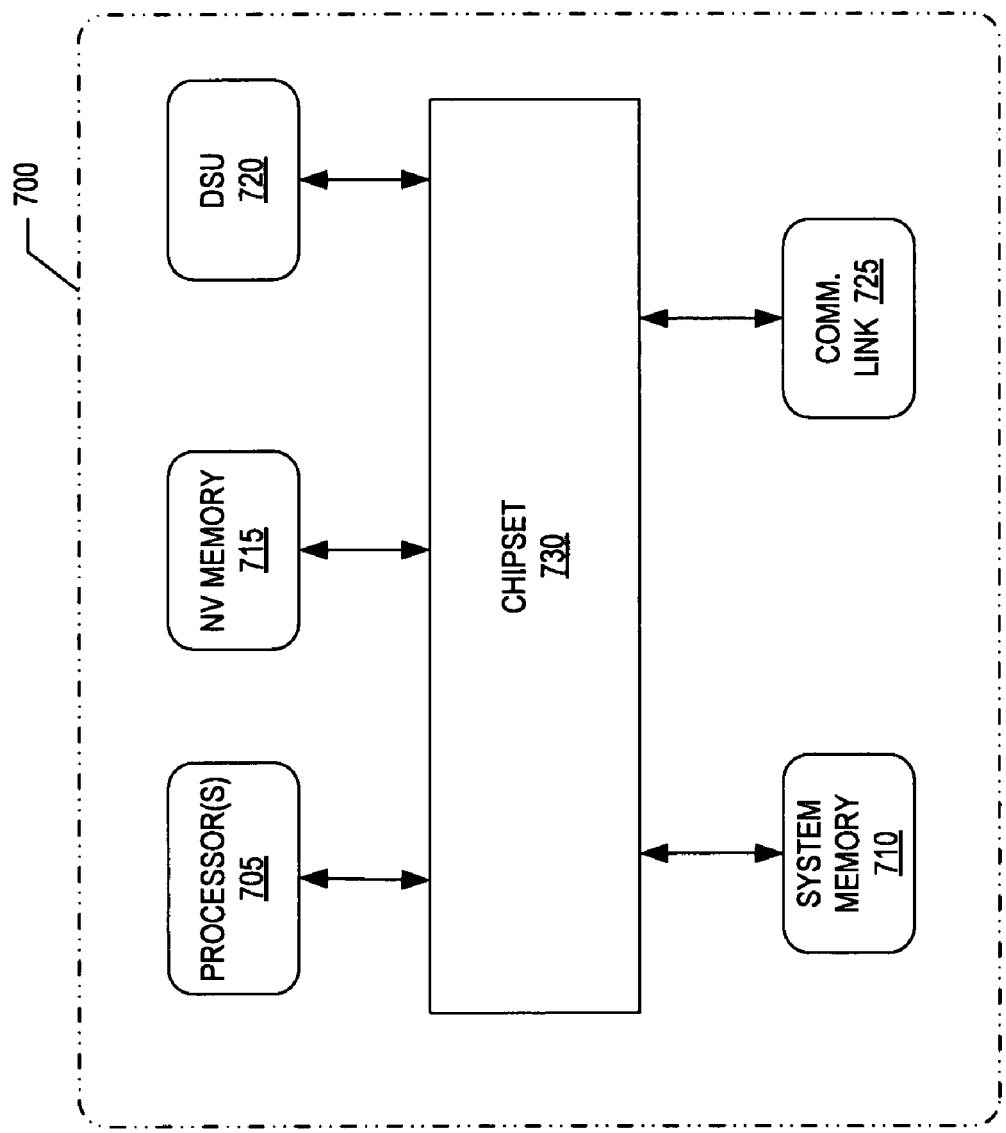
FIG. 7 is block diagram illustrating a demonstrative processing system implemented with an embodiment of the invention.

FIG. 7 is a block diagram illustrating a demonstrative processing system 700 for executing process 300. The illustrated embodiment of processing system 700 includes one or more processors (or central processing units) 705, system memory 710, nonvolatile (NV) memory 715, a data storage unit (DSU) 720, a communication link 725, and a chipset 730. The illustrated processing system 700 may represent a computing system including a desktop computer, a notebook computer, a workstation, a handheld computer, a server, a blade server, or the like.

The elements of processing system 700 are interconnected as follows. Processor(s) 705 is communicatively coupled to system memory 710, NV memory 715, DSU 720, and communication link 725, via chipset 730 to send and to receive instructions or data thereto/therefrom. In one example, NV memory 715 is a flash memory device. In other examples, NV memory 715 includes any one of read only memory (ROM), programmable ROM, erasable programmable ROM, electrically erasable programmable ROM, or the like. In one example, system memory 710 includes random access memory (RAM), such as dynamic RAM (DRAM), synchronous DRAM, (SDRAM), double data rate SDRAM (DDR SDRAM), static RAM (SRAM), and the like. DSU 720 represents any storage device for software data, applications, and/or operating systems, but will most typically be a non-volatile storage device. DSU 720 may optionally include one or more of an integrated drive electronic (IDE) hard disk, an enhanced IDE (EIDE) hard disk, a redundant array of independent disks (RAID), a small computer system interface (SCSI) hard disk, a serial advanced technology attachment (SATA or Serial ATA) and the like. Although DSU 720 is illustrated as internal to processing system 700, DSU 720 may be externally coupled to processing system 700. Communication link 725 may couple processing system 700 to a network such that processing system 700 may communicate over the network with one or more other computers. Communication link 725 may include a modem, an Ethernet card, a Gigabit Ethernet card, Universal Serial Bus (USB) port, a wireless network interface card, a fiber optic interface, or the like.

It should be appreciated that various other elements of processing system 700 have been excluded from FIG. 7 and this discussion for the purpose of clarity. For example, processing system 700 may further include a graphics card, additional DSUs, other persistent data storage devices (e.g., tape drive), and the like. Chipset 730 may also include a system bus and various other data buses for interconnecting subcomponents, such as a memory controller hub and an input/output (I/O) controller hub, as well as, data buses (e.g., peripheral component interconnect bus) for connecting peripheral devices to chipset 730. Moreover, processing system 700 may operate without one or more of the elements illustrated. For example, processing system 700 need not include DSU 720.

The processes explained above are described in terms of computer software and hardware. The techniques described may constitute machine-executable instructions embodied within a machine (e.g., computer) readable medium, that when executed by a machine will cause the machine to perform the operations described. Additionally, the processes may be embodied within hardware, such as an application specific integrated circuit ("ASIC") or the like.

A machine-accessible medium includes any mechanism that provides (i.e., stores and/or transmits) information in a form accessible by a machine (e.g., a computer, network device, personal digital assistant, manufacturing tool, any device with a set of one or more processors, etc.). For example, a machine-accessible medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method comprising:
    charging an interconnect with a switch in response to radiation incident upon the switch while the switch is in an open-circuit state, wherein the switch is coupled between the interconnect and a detector;
    monitoring charge on the interconnect; and
    generating a signal indicating presence of the radiation in response to the charge on the interconnect.

2. The method of claim 1, further comprising enabling the detector in response to the signal.

3. The method of claim 2, wherein enabling the detector comprises changing the switch from the open-circuit state to a closed-circuit state, the method further comprising reading an output from the detector via the interconnect in response to the signal.

4. The method of claim 3, further comprising resetting the charge on the interconnect prior to reading the output from the detector.

5. The method of claim 1, wherein monitoring the charge of the interconnect comprises monitoring for a voltage change on the interconnect.

6. The method of claim 5, further comprising resetting the voltage on the interconnect prior to monitoring for the voltage change on the interconnect.

7. The method of claim 1, wherein the interconnect is one of a plurality of interconnects, the switch is one of a plurality of switches, and the detector is one of a plurality of detectors, the method further comprising:
    connecting the plurality of interconnects to one another;
    charging the plurality of interconnects with the plurality of switches in response to radiation incident upon the plurality of switches while in the open-circuit state; and
    monitoring the charge on the plurality of interconnects; and
    generating the signal indicating presence of the radiation in response to the charge on the plurality of interconnects.

8. An apparatus comprising:
    an interconnect;
    a detector to detect radiation;
    a switch coupled between the interconnect and the detector to charge the interconnect in response to the radiation while the switch is in an open-circuit state; and
    control circuitry coupled to the interconnect to detect the charge on the interconnect and to generate a signal indicating presence of the radiation in response to the charge, wherein the control circuitry is further coupled to enable the detector in response to the signal by changing the switch from the open-circuit state to a closed-circuit state.

9. The apparatus of claim 8, wherein the control circuitry further comprises an edge detector coupled to detect a voltage change on the interconnect.

10. The apparatus of claim 8, wherein the control circuitry further comprises a reset circuit coupled to discharge the interconnect.

11. The apparatus of claim 8, wherein the switch comprises an n-type metal oxide semiconductor field effect transistor ("nMOSFET") coupled between the interconnect and the detector to charge the interconnect in response to the radiation incident upon a p-n junction of the nMOSFET.

12. The apparatus of claim 8, further comprising:
    a plurality of interconnects;
    a plurality of detectors to detect radiation; and
    a plurality of switches coupled between the plurality of interconnects and the plurality of detectors to charge the plurality of interconnects in response to the radiation while the plurality of switches are in an open-circuit state, wherein the control circuitry is coupled to connect the plurality of interconnects to one another, and to generate a signal indicating presence of the radiation in response to the charge on the plurality of interconnects.

13. The apparatus of claim 8, wherein the detector comprises:

a photodiode to accumulate charge in response to the radiation;

a reset coupled to remove the accumulated charge from the photodiode; and a buffer coupled between the photodiode and the switch to output an electrical characteristic representative of the accumulated charge on the photodiode via the interconnect.

14. The apparatus of claim 8, further comprising a scintillator disposed proximate to the detector to translate the radiation from a first wavelength to a second wavelength.

15. A system comprising:

a radiation source to emit radiation;

a plurality of interconnects;

a plurality of detectors to detect the radiation;

a plurality of switches coupled between the plurality of interconnects and the plurality of detectors to charge the plurality of interconnects in response to the radiation while the plurality of switches are in an open-circuit state; and control circuitry coupled to the plurality of interconnects to detect the charge and to generate a signal indicating presence of the radiation in response to the charge, wherein the control circuitry is further coupled to change the plurality of switches from the open-circuit state to a closed-circuit state in response to the signal.

16. The system of claim 15, wherein the control circuitry is further coupled to connect the plurality of interconnects to one another.

17. The system of claim 16, wherein the control circuitry is further coupled to discharge the plurality of interconnects.

18. The system of claim 17, wherein the control circuitry further comprises an edge detector coupled to detect a voltage change on the plurality of interconnects and to generate the signal in response to the voltage change.

19. The system of claim 18, wherein the control circuitry is further coupled to read an output from each of the plurality of detectors via the plurality of interconnects.

* * * * *